United States Patent [19]

Turner

[11] 4,268,519
[45] May 19, 1981

[54] METHOD OF TREATING OTITIS MEDIA
[75] Inventor: David M. Turner, Quorn, England
[73] Assignee: Fisons Limited, Suffolk, England
[21] Appl. No.: 147,917
[22] Filed: May 8, 1980
[30] Foreign Application Priority Data
  Jun. 5, 1979 [GB] United Kingdom .............. 19516/79
[51] Int. Cl.³ .............................................. A61K 31/35
[52] U.S. Cl. ................................................ 424/283
[58] Field of Search ......................................... 424/283
[56] References Cited
  U.S. PATENT DOCUMENTS 3,686,412  8/1972  Fitzmaurice et al. ............... 424/283
  3,720,690  3/1973  King et al. ....................... 424/283 X
  3,777,033  12/1973 Fitzmaurice et al. ............... 424/283
  3,975,536  8/1976  Stevenson et al. ................. 424/283
  4,029,761  6/1977  Kingsley .......................... 424/283 X
  4,067,992  1/1978  Kingsley et al. .................. 424/283
  4,146,634  3/1979  Brown et al. ..................... 424/283

4,152,448  5/1979  Wardell ........................... 424/283

*Primary Examiner*—Frank Cacciapaglia, Jr.
*Attorney, Agent, or Firm*—Merriam, Marshall & Bicknell

[57] ABSTRACT

There is described a method of treatment of secretory otitis media, which method comprises administration of a compound of the formula I:

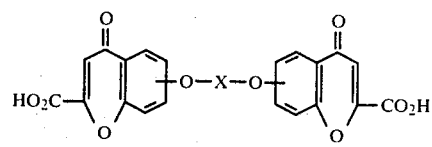

wherein X is a polymethylene chain containing 3 to 7 carbon atoms inclusive, which chain may be substituted by an —OH group, or a pharmaceutically acceptable salt, ester or amide thereof, to a patient having secretory otitis media.

7 Claims, No Drawings

METHOD OF TREATING OTITIS MEDIA

This invention relates to a new therapeutic method.

In U.S. Pat. No. 3,686,412 there are described a large number of bis-chromonyl compounds and their use in the treatment of asthma. These compounds are described as being administered preferably by way of inhalation.

Surprisingly we have now found that a selected group of these compounds are useful in the treatment of secretory otitis media, a condition which is usually treated by adenoidectomy, myringotomy with suction and the introduction of a grommet into the middle ear.

According to the invention there is provided a method of treatment of secretory otitis media, which method comprises administration of a compound of the formula I,

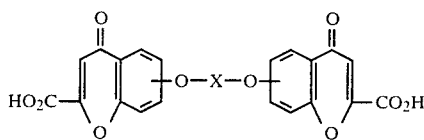

wherein X is a polymethylene chain containing 3 to 7 carbon atoms inclusive, which chain may be substituted by an —OH group, or a pharmaceutically acceptable salt, alkyl C 1 to 10 ester, mono-alkyl C 1 to 10 amide, di-alkyl C 1 to 10 amide or unsubstituted amide thereof, as active ingredient, to a patient having secretory otitis media.

Suitable pharmaceutically acceptable salts include, for example, ammonium salts, alkali metal salts (e.g. sodium, potassium and lithium), alkaline earth metal salts (e.g. magnesium and calcium), and salts with organic amines (e.g. mono- di- or tri- alkyl C 1 to 6 amines, piperidine, and trialkanol C 1 to 6 amine salts). Esters which may be mentioned include simple alkyl esters (e.g. methyl, ethyl, propyl, isopropyl, butyl and tertiary butyl esters) and amides which may be mentioned include simple amides (for example amides with ammonia and lower alkylamines such as methylamine, ethylamine etc).

The administration may be to the outer ear, e.g. to a patient whose ear drum is pierced and a grommet inserted. Alternatively and preferably the drug may be administered orally or intranasally.

In order to produce suitable compositions the drug is worked up with inorganic or organic pharmaceutically acceptable adjuvants, carriers or excipients. The type of formulation will vary with the mode of administration to be used. Examples of suitable adjuvants are for syrups, suspensions, dispersions or solutions: A liquid vehicle in which the active ingredients may be dissolved or suspended, e.g. water; and suspending agents, e.g. cellulose derivatives, gums etc.

The drug may, if desired, be used in a specific form, e.g. having a mass median diameter of less than 10 microns.

The drug may also be formulated as an aqueous, e.g. a water: chloroform (400:1), solution containing from 0.001 to 10.0% by weight of the drug. The free acids of formula I may conveniently be administered as an aqueous suspension containing from 0.1 to 10%, e.g. about 2% by weight of the drug.

We prefer liquid formulations which may, if desired, be sealed in the ear, e.g. with a plug. Liquid formulations may comprise excipients to help penetration of the outer ear. We also prefer liquid formulations, e.g. a sterile aqueous solution, or dry powder formulations, e.g. a mixture of fine active ingredient with coarse lactose for oral or nasal administration.

The dosage to be administered will of course vary with the method of administration, the condition to be treated and with its severity. However in general a dosage of from about 2 to 50, and more preferably 2 to 30 mg of the drug administered 1 to 8 times a day by the oral or intranasal route, or from 1 to 10 drops of a 0.1 to 10% w/w solution or suspension administered from 1 to 10, preferably 1 to 6 and most preferably 5 or 6 times a day, to each ear is found to be satisfactory.

Conditions which may be treated by the method of the invention include a secretory effusion into the middle ear, which may be asymptomatic save for deafness or which may be a consequence of bacterial infection. Secretory otitis media is sometimes known as serous otitis media.

The method of the invention is particularly applicable to children, e.g. children under the age of 8.

Specific examples of the group X are groups of the formula $-(CH_2)_5-$ and $-CH_2CHOHCH_2-$.

The chain —O—X—O— may link different or corresponding positions on the chromone nuclei.

A specific compound which may be used in this invention is 1,3-bis(2-carboxychromon-5-yloxy)-2-hydroxypropane. This compound may of course be used in the form of its pharmaceutically acceptable, e.g. its di-sodium, di-potassium, calcium, magnesium or di-piperidine salt. It may also be used in the form of its di-ethyl ester, or of its simple amide derived from ammonia.

The invention is illustrated, but in no way limited, by the following Example.

EXAMPLE

A study was conducted on 12 children, 3–7 years old, who had secretory otitis media.

The subjects were treated with the disodium salt of 1,3-bis(2-carboxychromon-5-yloxy)-2-hydroxypropane as a 2% solution applied by spray into the nasal cavities, six times a day, 2.5 mg per application.

At the onset of the study and again 1 month, 3 months, and 6 months later all children had an ear, nose and throat examination, pure tone and otoadmittance audiometry, and acoustic reflex test. Before treatment all children had a conductive hearing impairment of at least 20 dB, flat tympanometric curves, and absence of acoustic reflexes in both ears. Six months after starting the therapeutic schedule, improved hearing was recorded in 11 out of the 12 children. Flat tympanometric curve and/or absent acoustic reflexes persisted in 1 subject. Inadequate ventilation as demonstrated by increased negative pressure in the middle ear was observed in none of the children.

I claim:

1. A method of treatment of secretory otitis media, which method comprises administration of a compound of the formula I:

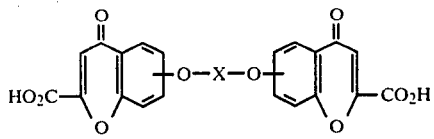

wherein X is a polymethylene chain containing 3 to 7 carbon atoms inclusive, which may be substituted by an —OH group, or a pharmaceutically acceptable salt, alkyl C 1 to 10 ester, mono-alkyl C 1 to 10 amide, di-alkyl C 1 to 10 amide or unsubstituted amide thereof, as active ingredient, to a patient having secretory otitis media.

2. A method according to claim 1, wherein the active ingredient is administered orally or intranasally.

3. A method according to claim 1, wherein the active ingredient is administered as a sterile aqueous solution.

4. A method according to claim 1, wherein from 2 to 50 mg of the active ingredient are administered from 1 to 8 times per day orally or intranasally.

5. A method according to claim 1, wherein the patient is a child under the age of 8.

6. A method according to claim 1, wherein the active ingredient is 1,3-bis(2-carboxychromon-5-yloxy)-2-hydroxypropane or a pharmaceutically acceptable salt thereof.

7. A method according to claim 6, wherein the active ingredient is the disodium salt of 1,3-bis(2-carboxychromon-5-yloxy)-2-hydroxypropane.

* * * * *